United States Patent [19]
Scheller et al.

[11] Patent Number: 5,370,658
[45] Date of Patent: Dec. 6, 1994

[54] MICROSURGICAL INSTRUMENT HAVING DEXTEROUS HANDLE WITH INTERCHANGEABLE INSTRUMENT HEADS

[75] Inventors: Gregg D. Scheller, Chesterfield; Kurt W. Gampp, Jr., Ellisville; Michael D. Auld, Ballwin, all of Mo.

[73] Assignee: Synergetics, Inc., Chesterfield, Mo.

[21] Appl. No.: 972,234

[22] Filed: Nov. 5, 1992

[51] Int. Cl.⁵ .................................................. A61B 17/32
[52] U.S. Cl. .................................. 606/205; 606/174
[58] Field of Search ............... 606/205–210, 606/167, 170, 171, 174, 175, 139, 142, 144

[56] References Cited

U.S. PATENT DOCUMENTS

| | | | |
|---|---|---|---|
| 2,165,374 | 7/1939 | Heilig | 606/210 |
| 2,898,915 | 8/1959 | Krammer | 606/139 |
| 4,165,745 | 8/1979 | Heifetz | 606/174 |
| 4,258,716 | 3/1981 | Sutherland | 606/174 |
| 4,433,687 | 2/1984 | Burke et al. | 606/174 |
| 4,598,711 | 7/1986 | Deniega | |
| 4,602,631 | 7/1986 | Funatsu | |
| 4,644,651 | 2/1987 | Jacobsen | 606/174 |
| 4,760,848 | 8/1988 | Hasson | 606/206 |
| 4,873,979 | 10/1989 | Hanna | 606/210 |
| 4,938,214 | 7/1990 | Specht et al. | 606/206 |
| 4,955,887 | 9/1990 | Zirm | 606/170 |
| 5,184,625 | 2/1993 | Cottone, Jr. et al. | 606/206 |

FOREIGN PATENT DOCUMENTS

| | | | |
|---|---|---|---|
| 1026461 | 4/1953 | France | 606/210 |
| 2091624 | 8/1982 | United Kingdom | 606/205 |
| 8200968 | 4/1982 | WIPO | 606/142 |

Primary Examiner—Ralph A. Lewis
Attorney, Agent, or Firm—Rogers, Howell & Haferkamp

[57] ABSTRACT

A microsurgical instrument is comprised of a handle and a plurality of interchangeable instrument heads. Each of the instrument heads is constructed to perform a microsurgical operation such as forcep clamping and scissors cutting in a plane parallel to a longitudinal axis of the instrument, and in a plane positioned at an angle relative to the longitudinal axis of the instrument. The instrument handle is comprised of an exterior surface formed as at least two lever arms that are manually manipulable laterally toward and away from the longitudinal axis of the instrument to control the surgical operation performed by the instrument head connected with the handle. Because the entire handle exterior surface is manipulated to operate the instrument head connected with the handle, the instrument need not be held at any specific orientation relative to the hand in order to easily operate the instrument head by manipulating the fingers of the hand.

33 Claims, 3 Drawing Sheets

MICROSURGICAL INSTRUMENT HAVING DEXTEROUS HANDLE WITH INTERCHANGEABLE INSTRUMENT HEADS

BACKGROUND OF THE INVENTION

1. Field of the Invention

The present invention relates to a microsurgical instrument comprised of a handle and a plurality of interchangeable instrument heads. Each of the instrument heads are constructed to perform microsurgical operations such as forcep clamping and scissors cutting in a plane oriented at an angle to a longitudinal axis of the instrument, and in a plane parallel to the longitudinal axis of the instrument. The instrument handle is comprised of an exterior surface formed as at least two lever arms that are manually manipulable laterally toward and away from the longitudinal axis of the instrument to control the surgical operation performed by the instrument head connected with the handle. Because the entire handle exterior surface is manipulated to operate the instrument head connected with the handle, the instrument need not be held in any specific orientation relative to the hand in order to easily operate the instrument head by manipulating the fingers of the hand.

2. Description of the Related Art

Many different types of microsurgical instruments are known in the prior art. By the term "microsurgical instrument" what is meant is those types of instruments employed in performing surgical operations on extremely small and extremely delicate parts of the human anatomy. These instruments are specifically designed with an operative tip that is inserted into the anatomy through a very small incision. The surgical procedures performed by the instrument tip are typically observed by the surgeon through a microscope or endoscope of some type. One example of this type of surgery is ophthalmic surgery.

Typical microsurgical instruments are comprised of a manual handle having an instrument head secured to one end. The instrument head has a hollow tube projecting therefrom, and a rod received in the tube interior. The rod and tube are caused to move relative to each other in response to manual manipulation of some type of actuator on the instrument handle, and the relative movement of the rod and tube operates a surgical implement formed at their distal ends.

A common disadvantage encountered in the use of prior art microsurgical instruments is that the manual actuator positioned on the instrument handle is not conveniently accessible by the fingers of the surgeon for all positions of the handle in the surgeon's hand. In microsurgical operations it is often necessary to rotate the instrument in the surgeon's hand. With a manual actuator provided on only one side of the handle, rotating the handle so that the actuator is moved away from easy access by the surgeon's fingers makes it difficult to manipulate the actuator. To overcome this advantage, prior art microsurgical instruments have been developed where the instrument head is rotatable relative to the handle. With instruments of this type, the handle is held in a stationary position in the surgeon's hand and the instrument head is rotated relative to the handle to rotate the surgical implement formed at the distal end of the instrument head tube and rod. However, this type of instrument has also been found to be disadvantaged in that it requires two hands to rotate the instrument head during a surgical operation. The surgeon's hand gripping the instrument handle must be held stationary while a second hand, either of the surgeon or an assistant, rotates the instrument head in order to reposition the surgical implements formed at the distal ends of the tube and rod.

It is an object of the present invention to overcome the disadvantages associated with prior art microsurgical instruments by providing a microsurgical instrument with interchangeable instrument heads, each head being configured to perform a different surgical operation, wherein each of the heads is releasably attachable to a handle that may be rotated in the hand of the surgeon to rotate the surgical implement of the instrument head. The handle comprises lever arms that are easily manipulated in any position of the handle in the surgeon's hand to control operation of the surgical instruments of the implement head.

SUMMARY OF THE INVENTION

The microsurgical instrument of the present invention is basically comprised of a handle assembly and a plurality of instrument head assemblies that are releasably attachable to the handle assembly. In the preferred embodiments of the invention the component parts of the handle assembly and of the separate instrument heads are all constructed of materials capable of being sterilized.

The instrument handle is comprised of a center column extending longitudinally along the handle between its opposite ends, and an exterior sleeve surrounding the center column and secured to the center column at the columns first end. A pair of longitudinal slots are cut in the sleeve at diametrically opposite positions on the sleeve. The pair of slots extend along a portion of the sleeves longitudinal length from the end of the handle releasably attached to the instrument head. The slots form a pair of lever arms in the sleeve, each lever arm having a semi-circular cross section. A pair of oblong apertures are also formed in the sleeve, each positioned between the pair of slots. Together the slots and apertures cause the lever arms formed in the sleeve to resiliently flex away from each other and away from the center longitudinal axis of the handle.

The handle center column is provided with an internal bore at the end of the handle attachable to the instrument heads. A reciprocating handle piston is received in the bore and a mechanical linkage is provided between the piston and the pair of lever arms formed in the exterior sleeve of the handle. By manually manipulating the pair of lever arms so that they reciprocate laterally toward and away from the center axis of the handle, the handle piston is caused to reciprocate along the handle center axis through the handle interior bore.

Each of the plurality of instrument heads of the invention is configured to be releasably attached to the end of the handle adjacent the reciprocating handle piston. Each of the instrument heads has a hollow interior bore and a head piston received in the bore for reciprocating movement along a center axis of the instrument head. When each one of the instrument heads of the invention is attached to the instrument handle, the head piston engages against the handle piston and reciprocating movement of the handle piston causes the reciprocating movement of the head piston inside the internal bore of the instrument heads. A narrow tube projects from each of the instrument heads and a narrow rod extends through the center bore of the tube.

The distal ends of the tube and rod of each of the instrument heads of the invention are formed as surgical forceps or scissors that operate in response to relative linear or rotary movement between the tube and rod. In each of the instrument heads of the invention, a mechanical connection is provided between the tube and rod of the instrument head and the head piston, whereby reciprocating movement of the head piston in the instrument head produces relative linear or rotational movement between the tube and rod of the head.

In the manner described above, the microsurgical instrument of the present invention provides an instrument handle that is capable of being attached to a plurality of different instrument heads, each capable of performing a forcep clamping or scissors cutting microsurgical operation. The handle is designed with an exterior surface that can be easily rotated about its center axis in a single hand of a surgeon holding the instrument, and the handle exterior may be manipulated by the surgeon's hand laterally toward and away from the center axis of the handle to perform the particular surgical operation of the instrument head attached to the handle.

BRIEF DESCRIPTION OF THE DRAWINGS

Further objects and features of the present invention are revealed in the following detailed description of the preferred embodiments of the invention and in the drawing figures wherein.

DESCRIPTION OF THE PREFERRED EMBODIMENTS

Figures 1, 2:
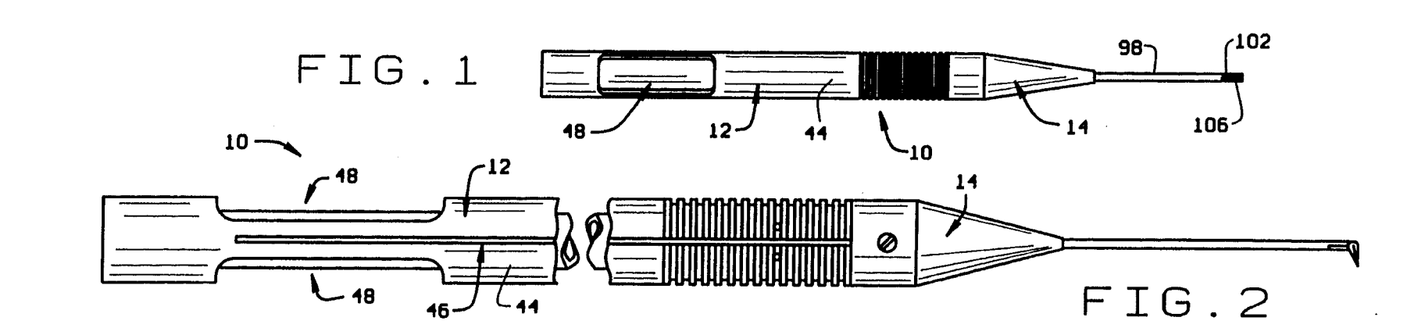
FIG. 1 is a plan view of the microsurgical instrument of the present invention.
FIG. 2 is a side elevation view of the instrument handle and one of the plurality of instrument heads that make up the microsurgical instrument of the invention.

FIG. 1 shows the microsurgical instrument 10 of the present invention. As seen in FIG. 1, the instrument is generally comprised of an instrument handle 12 and one of a plurality of instrument heads 14 releasably attached to the handle. In the preferred embodiments of the invention all of the component parts of the instrument handle and instrument head to be described are constructed of a material that is capable of being sterilized, preferably alloys of titanium or aluminum to reduce the instrument's weight. However, it should be understood that the preferences set forth herein are not intended to be limiting and the instrument of the invention may be constructed from a variety of materials suitable for the purposes herein described.

Figure 5:
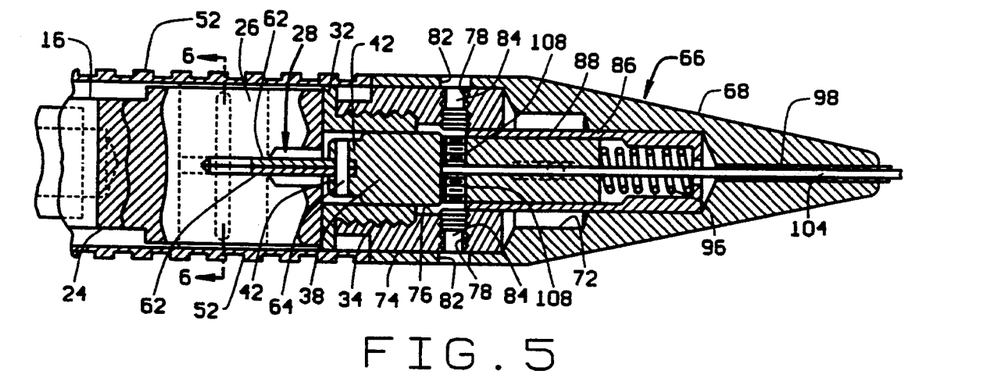
FIG. 5 is a partial plan view in section of the surgical instrument taken along the line 4—4 of FIG. 3.

The instrument handle 12 is comprised of a center tubular column 16 in its interior. A rear plug 18 is press fit into a rearward end, or left hand end as viewed in the drawing figures, in the center column. The rear plug 18 is comprised of a smaller diameter land 20 that is press fit into the rearward end of the center column 16 and a larger diameter land 22 positioned adjacent the rearward end of the column. A forward plug 24 is press fit into the forward end, or right hand end, of the center column 16. The forward plug 24 is formed with a generally planar central web 26 that projects forward from the plug parallel to the center axis of the handle center column 16. As best seen in FIG. 5, the central web 26 has a stepped slot 28 cut therethrough. The slot 28 has two different lateral widths, with the smaller of the two widths being large enough to accommodate the insertion of two link members yet to be described. The forward plug 24 has an annular disc 32 formed integrally to its right hand end as viewed in the drawing figures. The annular disk 32 is formed with an external diameter substantially equal to the internal diameter of a handle sleeve yet to be described. A hollow neck 34 is formed integrally on the right hand surface of the annular disk 32 opposite the disk's connection to the central web 26. The neck 34 is cylindrical and has a screw thread formed over its exterior surface. A hollow cylindrical bore 36 extends completely through the center of the handle neck 34 and annular disk 32 and communicates with the void formed in the stepped slot 28 of the central web 26. The annular disk 32, the handle neck 34 and the bore hole 36 extending through the interior of the neck are all coaxial to the center axis of the handle center column 16. A handle piston 38 is received for reciprocating longitudinal movement within the neck interior bore 36. The piston 38 is formed with a cylindrical piston head having a diameter slightly smaller than the diameter of the neck interior bore 36 to enable easy sliding reciprocating movement of the piston within the bore along the center axis of the center column 16. Spaced flanges 42 are formed at the left hand end of the piston or the end of the piston facing the central web 26. The purpose served by the spaced flanges is yet to be described.

From the construction of the instrument handle described above, it can be seen that the rear plug 18, the center column 16, and the forward plug 24 with the central web 26, annular disk 32 and cylindrical neck 34 are all connected securely and stationary relative to each other as a single unit of the instrument handle 12. The handle piston 38 is received in the interior bore of the handle neck 34 for reciprocating sliding movement longitudinally along the center axis of the center column 16 and instrument handle 12.

A cylindrical sleeve 44 having a hollow interior bore extending between its opposite ends is assembled over the center column 16 of the instrument handle. As seen in the drawing figures, a rearward end, or left hand end, of the sleeve 44 is press fit over the larger diameter land 22 of the rear plug 18 with the center column 16, forward plug 24 and handle piston 38 contained in the interior of the sleeve 44. The interior diameter of the sleeve is chosen to securely hold the larger diameter land 22 of the rearward plug in the sleeve interior without the need for brazing or other similar types of connection. However, these other types of connection may also be employed to secure the sleeve to the rear plug land 22. The sleeve 44 is assembled on the rear plug 18 so that it is positioned coaxial to the center column 16. A pair of longitudinal slots 46 are cut in diametrically opposite sides of the sleeve. The slots 46 are cut through the sleeve beginning at the right hand end of the sleeve and terminate short of the left hand end of the sleeve. A pair of oblong apertures 48 are also cut through the sleeve on diametrically opposite sides of the sleeve. As seen in the drawing figures, the pair of apertures 48 are cut through portions of the sleeve wall between the pair of slots 46 cut through the sleeve and adjacent the left hand ends of the slots. The pair of slots 46 cut in the sleeve form the sleeve into a pair of resilient lever arms 52, each having a semicircular cross section. The oblong apertures 48 are cut through the sides of the sleeve adjacent the left hand ends of the slots 46 and the lever arms 52 formed in the sleeve are bent laterally outward away from the center axis of the instrument handle to the at rest positions of the lever arms shown in FIG. 4. By forming the lever arms 52 in this manner the arms may be manually manipulated to move laterally or radially inward toward each other and toward the center axis of the instrument handle in response to the fingers of a surgeon exerting a force on the exterior surface of the sleeve, and may resiliently bias outward away from each other and the center axis of the instrument handle in response to the force of the surgeon's fingers being removed from the exterior surface of the sleeve.

Figure 6:
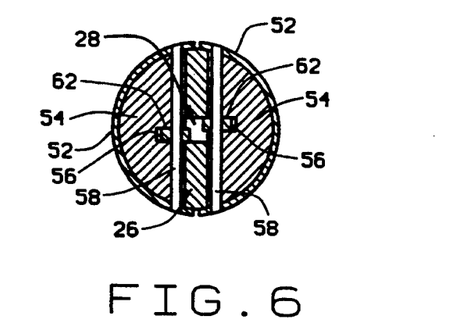
FIG. 6 is an end view in section taken along the line 6—6 of FIG. 5.

A pair of pivot blocks 54, are secured to the interior surface of the sleeve 44. The pivot blocks are secured in the semicircular voids in the interiors of the pair of lever arms 52 formed in the sleeve. The pivot blocks 54 are secured to the interior surfaces of the lever arms 52 on opposite sides of the forward plug central web 26. Each pivot block 54 is formed with a longitudinal slot 56 therein and a lateral pivot pin 58 traversing the slot. The pivot pins 58 also serve to secure the blocks 54 to the interior surfaces of the lever arms 52. As is best seen in FIGS. 5 and 6, the longitudinal slots 56 of the pivot blocks 54 are not positioned in the same lateral plane directly opposite each other but are slightly askew to accommodate a pair of links yet to be described.

Figures 3, 4:
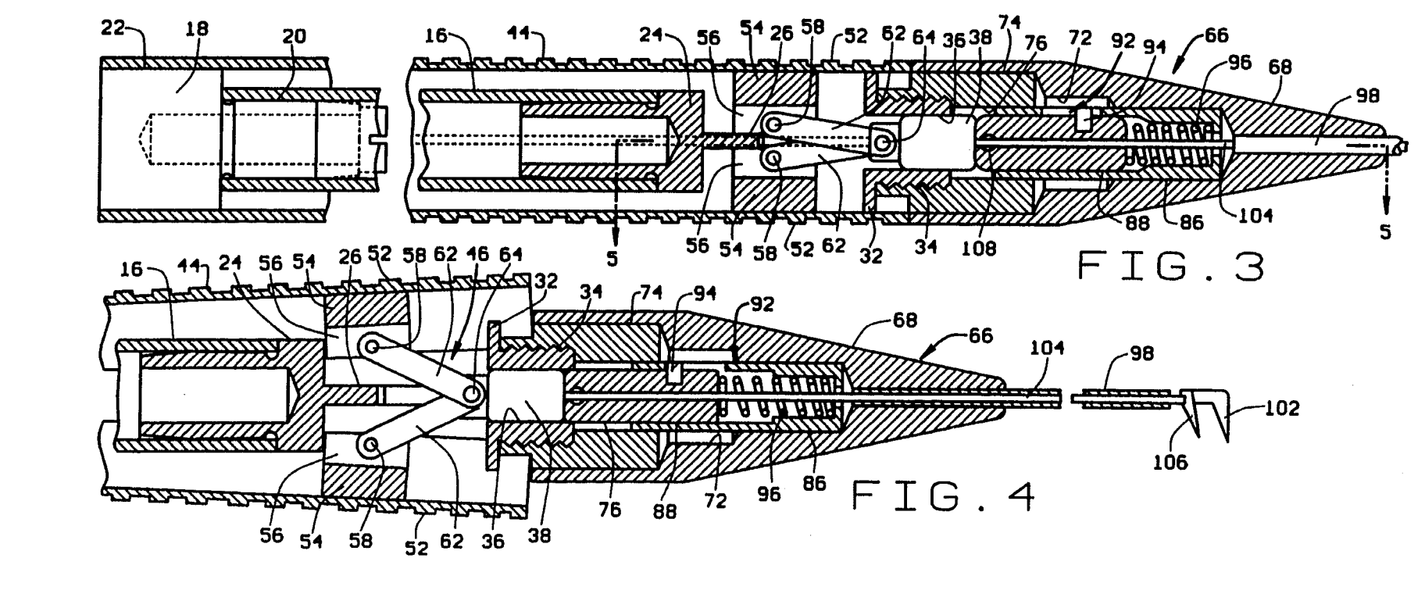
FIG. 3 is a segmented side elevation view in section of the surgical instrument of FIG. 2.
FIG. 4 is a partial side elevation view in section of the surgical instrument of FIG. 2.

The pair of links 62 referred to above have the same length and width, the width being chosen to fit easily within the pivot block slots 56 and with the combined link width fitting easily within the space between the handle piston flanges 42. The left hand ends of the two links 62 as viewed in FIG. 3-5 are secured for pivoting movement relative to the pivot blocks 54 by the pivot pins 58. The opposite right hand ends of the two links 62 are secured for pivoting movement relative to the left hand end of the handle piston 38 by a single pivot pin 64 inserted through the spaced flanges 42 of the piston and the right hand ends of the links 62.

From the description of the mechanical connection between the handle piston 38 and handle lever arms 52 provided by the links 62 described above, it can be seen that as the lever arms 52 are resiliently biased to their at rest positions relative to the handle center axis shown in FIG. 4, the links 62 pull the handle piston 38 to the left through the handle neck interior bore 36 to its position relative to the bore shown in FIG. 4. When the lever arms 52 are pressed against their bias toward each other and toward the instrument handle center axis to their extreme compressed relative positions shown in FIG. 3, the pair of links 62 connected between the lever arms 52 and the handle piston 38 will push the piston to the right through the handle neck interior bore 36 to its position relative to the bore shown in FIG. 3. By constructing the lever arms 52 which operate the reciprocating movement of the handle piston 38, from longitudinally split halves of the handle sleeve 44, it can be seen that the instrument handle of the present invention may be rotated in the hand of a surgeon to a variety of positions relative the surgeon's fingers while still enabling the surgeon to easily manipulate the lever arms 52 formed in the handle sleeve by compressing the lever arms toward each other and allowing the lever arms to spring back to their at rest positions and thereby reciprocate the handle piston 38 through the interior bore of the handle neck 34. The plurality of instrument heads 14 of the present invention are all designed to perform surgical operations in response to the selective reciprocating movement of the handle piston 38 controlled by the surgeon's hand.

A first embodiment of an instrument head employed with the instrument handle of the present invention is shown in FIGS. 1-5 of the drawing figures. This first instrument head 66 is constructed to perform a scissors cutting microsurgical operation where the cutting blades of the scissors are arranged to cut through a plane oriented at an angle relative to the longitudinal axis of the instrument handle 12. The instrument head 66 is comprised of a head housing 68 containing the component parts of the instrument. The housing 68 has an exterior shaped in a general cone configuration with the housing coming to a rounded point at its right hand end as viewed in the drawing figures, and the base of the housing at its left hand end having a cylindrical exterior surface with an exterior diameter substantially equal to the exterior diameter of the handle sleeve 44 with the lever arms 52 compressed to their furthest extent as shown in FIG. 3. A hollow bore 72 comprised of four internal cylindrical sections each having a different internal diameter measure is formed through the center of the head housing 68. A first cylindrical insert 74 is press fit into the left end of the housing internal bore 72 and is held securely in a tight friction engagement in the internal bore. The first insert has a hollow internal bore 76 extending through its center with a left hand portion of the bore having an internal screw thread formed therein. The internal screw thread of the bore 76 is determined to thread over the external screw thread of the handle neck 34 and thereby releasably secure the instrument head 66 to the instrument handle 12. The first insert 74 also has a pair of lateral screw threaded bores 78 extending through the insert on diametrically opposite sides of the insert. These bore holes 78 align coaxially with a pair of bore holes 82 provided in diametrically opposite sides of the head housing 68. The bore holes 82 in the head housing permit the insertion of small screws 84 into the bore holes and permit the screw threading of the screws 84 into the threaded bore holes 78 of the first insert to hold the insert securely within the head housing internal bore. However, these screws 84 are inserted as a last step of the assembly of the instrument head 66 as will be further explained.

A second tubular insert 86 is received in the head housing internal bore 72 and is slip fit and securely held in friction engagement in the third cylindrical section of the housing internal bore. The second insert 86 has a cylindrical interior bore and a head piston 88 is received within the bore of the second insert 86 for longitudinally reciprocating sliding movement therein. A longitudinal slot 92 is formed through the side of the second insert 86 and a limit pin 94 secured in a side of the head piston 88 engages in the slot 92 and limits the longitudinal reciprocating movement of the head piston in the second insert. A coil spring 96 is positioned between the right hand end face of the head piston 88 as viewed in the drawing figures and the right hand end wall of the second insert 86. The spring 96 biases the head piston 88 to the left as viewed in the drawing figures.

A narrow hollow tube 98 is press fit and securely held in the fourth cylindrical section of the head housing internal bore 72 and projects out from the tip of the instrument head 66. The press fit engagement of the tube 98 in the head housing 68 securely holds the tube in friction engagement with the housing. The external diameter of the tube 98 is preferably about 0.89 mm to enable the tube to be inserted into very small incisions for preforming microsurgical operations with the surgical implements formed at the distal end of the tube yet to be described. At the distal, right hand end of the tube 98 as viewed in the drawing figures, on one half of the tube wall is secured one blade of a scissors 102, the blade being positioned to perform a scissors cutting microsurgical operation across a plane arranged at an angle relative to the longitudinal axis of the instrument handle 12. In the preferred embodiment the one blade 102 is secured to the half of the tube end by a brazed, butt-joint connection. The friction engagement of the tube 98 in the head housing internal bore 72 holds the scissors blade 102 stationary relative to the head housing 68 and the instrument handle 12.

A narrow, cylindrical rod 104 is received for reciprocating, longitudinally linear movement inside the internal bore of the narrow tube 98. The distal, right hand end of the rod 104 as viewed in the drawing figures is formed in the configuration of the second scissors blade 106. When the rod 104 is caused to move in a longitudinally linear movement relative to the narrow tube 98 the scissors blade 106 formed on the end of the rod slides adjacent the scissors blade 102 formed on the end of the tube and together they perform a scissors cutting microsurgical operation across a plane oriented at an angle relative to the longitudinal axis of the instrument handle 12. The left hand end of the rod 104 projects from the tube 98 into the interior of the head housing 68 and extends through the end wall of the second insert 86, the coil spring 96, and through an internal bore extending longitudinally through the center of the head piston 88. As best seen in FIG. 5, a set screw 108 is screw threaded into one of a pair of threaded bore holes provided in diametrically opposite sides of the head piston 88. The set screw 108, and the complementary bore holes in the head piston 88 are dimensioned smaller than the threaded bore holes 78 in the first insert 74 to enable the set screw 108 to pass through the insert bore holes 78 and be screw threaded into one side of the head piston 88. Completely tightening down the set screw 108 in one of the bore holes 78 of the head piston 88 secures the left hand end of the rod 104 in the head piston 88.

After the set screw 108 has been screw threaded into one of the bore holes provided in the head piston 88 and the left hand end of the rod 104 is securely held in the interior bore of the head piston, then the pair of screws 84 are screw threaded into the bore holes 78 of the first insert 74 through the holes 82 provided for the screws in the head housing. This completes the assembly of the first instrument head.

In operation of the first instrument head 66 secured to the instrument handle 12 of the invention, the at rest position of the component parts of the head and handle are shown in FIG. 4. In their at rest positions, the lever arms 52 of the instrument handle 12 are resiliently biased laterally outward from the center axis of the handle, pulling the handle piston 38 to the left in the handle neck interior bore 36. With the instrument head 66 screw threaded onto the handle neck 34, the coil spring 96 biases the head piston 88 to the left as viewed in the drawing figures. The leftward movement of the piston 88 is limited by the engagement of the limit pin 94 in the longitudinal slot 92 of the second insert 86, but the longitudinal dimensions of the slot and head piston are chosen so that the head piston in its at rest position will engage against the handle piston with the instrument head screw threaded on the instrument handle. In the at rest position of the head piston 88 shown in FIG. 4, the rod 104 is pulled to the left and the scissors blade 106 formed on the right hand rod end is displaced from the scissors blade 102 formed on the right hand tube end, opening the microsurgical scissors implement formed by the two blades.

By compressing the pair of lever arms 52 of the instrument handle toward the center longitudinal axis of the handle, the pair of links 62 connected between the arms and the handle piston 38 push the piston to the right through the interior bore 36 of the handle neck 34. The handle piston 38 engages against the head piston 88 and the rightward movement of the handle piston through the handle interior bore 36 causes the head piston to move to the right through the interior bore of the second insert 86 in the head housing 68. The rightward movement of the head piston 88 is limited by the engagement of the limit pin 94 in the longitudinal slot 92 of the second insert. The rightward movement of the head piston 88 causes the narrow rod 104 to move in a longitudinally linear motion through the interior of the narrow tube 98 and causes the second scissors blade 106 formed on the right hand end of the rod 104 to slide adjacent over the first scissors blade 102 formed on the right hand end of the tube 98, thereby performing a microsurgical scissors cutting operation with the scissors implement formed at the right hand ends of the rod and tube. Releasing the instrument handle lever arms 52 allowing them to be resiliently biased laterally outward from the center axis of the handle and return to their at rest positions shown in FIG. 4 causes the scissors blades 106, 102 to open again.

In a variation of the first instrument head 66 described above, the scissors blades 102, 106 may be replaced with a pair of opposed clamping jaws of a forceps where the jaw surfaces engage across a plane oriented at an angle relative to the longitudinal axis of the instrument handle 12. The operation of the forceps jaws is substantially identical to that of the scissors blades described above.

Figure 7:
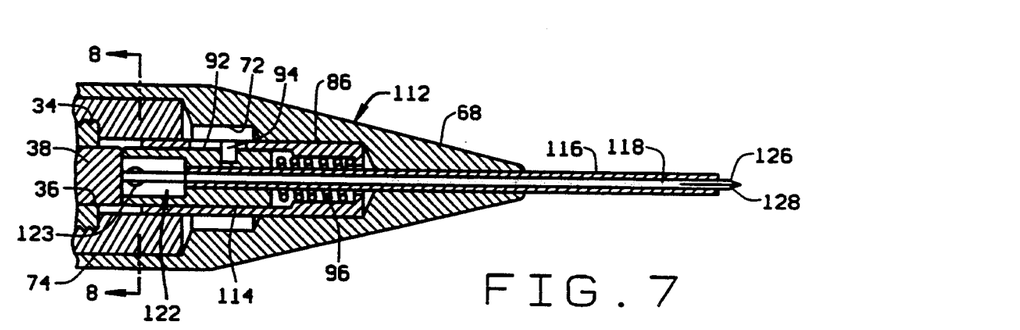
FIG. 7 is a partial elevation view in section of a second embodiment of the instrument head of the invention.
Figure 8:
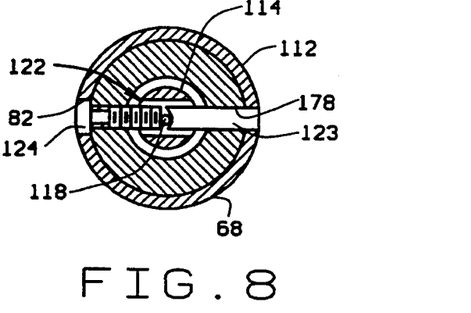
FIG. 8 is an end view in section taken along the line 8—8 of FIG. 7.
Figure 9:
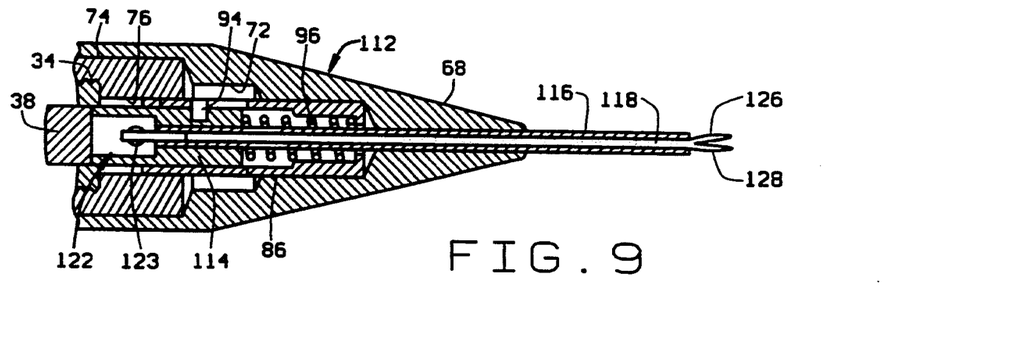
FIG. 9 is a partial elevation view in section of the embodiment of the instrument head shown in FIG. 7.
Figure 10:
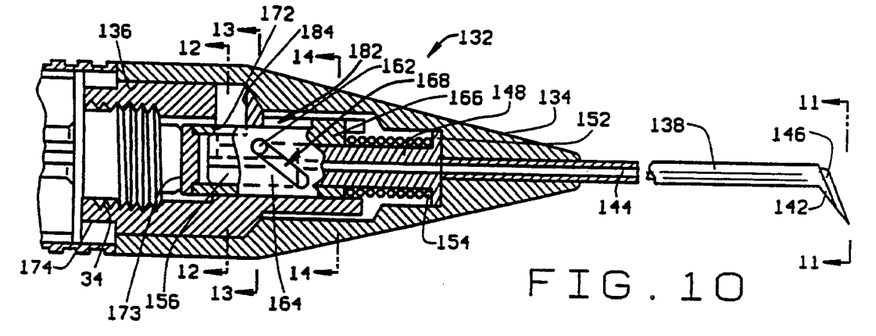
FIG. 10 is a partial elevation view in section of a third embodiment of the instrument head of the present invention.
Figures 11, 12, 13, 14, 15:
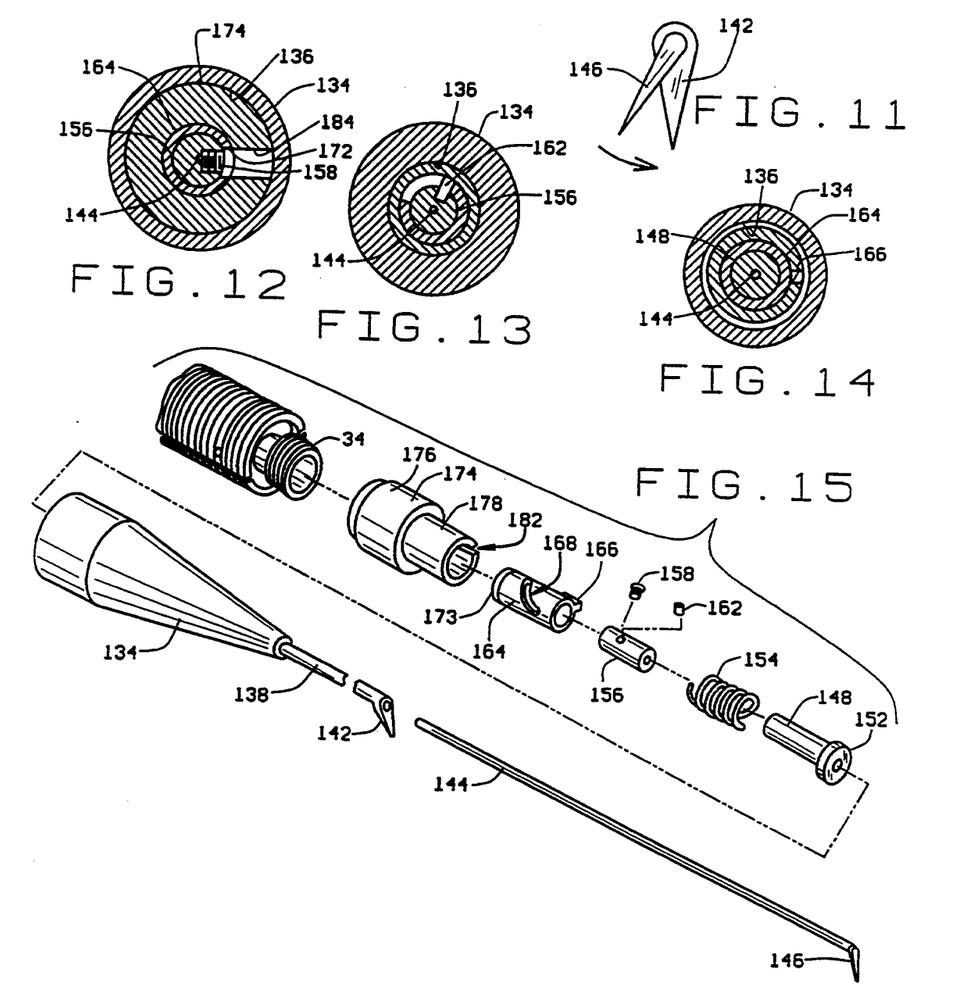
FIG. 11 is a detailed view of a third embodiment of the surgical implement taken along the line 11—11 of FIG. 10.
FIG. 12 is an end view in section taken along the line 12—12 of FIG. 10.
FIG. 13 is an end view in section taken along the line 13—13 of FIG. 10.
FIG. 14 is an end view in section taken along the line 14—14 of FIG. 10.
FIG. 15 is a partial assembly view of the embodiment of the instrument head of the invention shown in FIG. 10.

A second embodiment of the instrument head 112 of the invention is shown in drawing FIGS. 7-9. This embodiment has a microsurgical forceps formed as its surgical implement at the right hand ends of the tube and rod. Many of the component parts of the instrument head 112 shown in FIGS. 7-9 are identical to component parts of the first embodiment of the instrument head 66 and these same component parts have the same reference numerals employed in describing those parts with reference to the first embodiment of the instrument head. In comparison to the first embodiment of the instrument head, the second embodiment also includes a head housing 68, an internal bore 72 extending through the interior of the head housing and having four cylindrical sections each with different internal diameters, a first insert 74 with an internal bore 76 extending through the first insert. The first insert 74 is held in the internal bore 72 of the head housing 68 of this second embodiment of the instrument head in substantially the same manner as the insert of the first embodiment of the instrument head. A second insert 86 is also slip fit in the internal bore 72 of the head housing 68 of the second embodiment. The second insert 86 has the same construction as that of the first embodiment of the instrument head. The second insert also contains a coiled spring 96 in an identical manner to that of the first instrument head embodiment. The second instrument head differs from the first instrument head in the construction of the head piston 114 and the construction of the narrow tube 116 and narrow rod 118 extending from the right hand end of the head housing 68.

As seen in drawing FIGS. 7-9, the head piston 114 of the second embodiment of the instrument head is the same as that of the first embodiment in that it has a cylindrical configuration and is received for longitudinally reciprocating movement in the interior of the second insert 86. The head piston 114 is also provided with a limit pin 94 that engages in the longitudinal slot 92 of the second insert 86 and limits the longitudinal reciprocating movement of the head piston 114 in the internal bore of the second insert. The coil spring 96 engages against the right hand end face of the head piston 114 at one end and against the end wall of the second insert 86 at its opposite end to bias the head piston to the left as viewed in the drawing figures.

The head piston 114 of the second embodiment differs from the head piston of the first embodiment in that the left hand end of the hollow narrow tube 116 is secured by a press fit friction engagement in the internal bore of the head piston. With the tube 116 attached to the head piston 114 in this manner it reciprocates longitudinally along the center axis of the instrument handle 12 with reciprocation of the head piston along this axis. The second embodiment of the head piston 114 further differs from the head piston of the first embodiment in that a lateral slot 122 is formed through the left hand end of the head piston. The lateral slot 122 is positioned relative to the head piston so that it aligns with the pair of diametrically opposed bore holes through the head housing 82 and through the first insert 78.

The narrow rod 118 is received in the interior of the narrow tube 116 for reciprocating longitudinally linear movement therein. The left hand end of the rod 118 projects from the left hand end of the tube 116 into the lateral slot 122 of the head piston. A cylindrical pin 123 with a V-shaped notch at its distal end is inserted through aligned bore holes 82 and 78 of the head housing and first insert, respectively. The pin is held securely in friction engagement in the bore holes and the V-notch of the pin engages against one side of the rod 118 left end. A screw 124 is screw threaded through the opposite aligned bore holes 82, 78 of the head housing and first insert, respectively, and engages against the opposite lateral side of the rod left end from the pin 123, thereby securing the rod 118 stationary relative to the head housing 82. From this described construction, it can be seen that as the head piston 114 is reciprocated along the center axis of the handle 12, the tube 116 reciprocates along the axis with the piston and both the piston and tube reciprocate longitudinally in the head housing relative to the stationary rod 118.

At the right hand end of the rod 118, the rod is longitudinally split forming a pair of forcep jaws in the rod end. The forcep jaws 126, 128 are resiliently bent outward so that when the tube 116 is moved to the left in response to head piston 114 movement to the left, the forcep jaws project from the end of the tube and open as seen in FIG. 9. When the tube is moved to the right in response to head piston movement to the right, the right tube end causes the forcep jaws to close.

With the handle lever arms 52 at their at rest positions shown in FIG. 4, the handle piston 38 is retracted to the left in the neck interior bore 36 and the coil spring 96 of the instrument head 112 biases the head piston 114 to the left as viewed in FIG. 9. The leftward movement of the head piston 114 retracts the right hand end of the narrow tube 116 from its engagement over the right hand end of the rod 118 and uncovers the pair of forcep jaws 124, 126 formed in the right hand end of the rod. This enables the resiliency of the forcep jaws to open the jaws as shown in FIG. 9. As the lever arms 52 of the instrument handle are compressed laterally toward the central axis of the handle 12, the handle piston 38 is pushed to the right through the interior bore of the handle neck 34 and pushes the head piston 114 to the right against the bias of the coil spring 96. The movement of the head piston 114 to the right pushes the hollow tube 116 to the right over the stationary rod 118, causing the right hand end of the tube 116 to pass over the open jaws formed at the right hand end of the rod 118 causing the jaws to close as shown in FIG. 7 to grip an object between the jaws. In this manner, the second embodiment of the instrument head 112 is employed with the previously described instrument handle 12 to perform microsurgical forcep gripping operations employing the forcep implement formed at the right end of the rod 118.

In a variation of the second instrument head embodiment 112 described above, the forcep jaws 126, 128 may be replaced by a pair of opposed scissors blades where the scissors blades slide across each other and perform a scissors cutting operation across a plane oriented parallel relative to the longitudinal axis of the instrument handle 12. The operation of the scissors blades is substantially identical to that of the forcep jaws described above.

FIGS. 10-15 show a third embodiment of the instrument head 132 of the present invention designed to be employed with the previously described instrument handle 12. This embodiment of the instrument head 132 is used in performing microsurgical scissors cutting operations where the scissors of the instrument cut across a plane positioned parallel to the longitudinal axis of the instrument handle.

The third embodiment of the instrument head 132 is comprised of a head housing 134 having an exterior configuration substantially identical to that of the first two embodiments of the instrument heads. The head housing also has an internal bore formed between the left and right hand ends of the housing, the internal bore having four interconnected cylindrical sections, each of different internal diameter. A narrow hollow tube 138 is press fit into the housing head internal bore 136 from the right hand end of the housing as viewed in the drawing figures. The left hand end of the tube 138 is securely held in friction engagement inside the housing bore. The right hand end of the tube 138 has one blade 142 of a surgical scissors formed thereon. As seen in the drawing figures, the scissors blade 142 formed at the distal end of the narrow tube 138 is positioned relative to the tube to perform a surgical scissors cutting operation across a plane substantially parallel to the center axis of the instrument handle 12 and the third embodiment of the instrument head 132.

A narrow rod 144 is inserted through a center bore hole of the tube 138 and the left hand end of the rod projects from the left end of the tube into the head housing internal bore 136. The rod is received in the tube bore for rotational movement relative thereto but is prevented from moving in a longitudinally linear direction relative to the tube as will be explained. The right hand end of the rod 144 is formed in the configuration of a second scissors blade 146. With the rod inserted in the interior of the tube 138, the rod scissors blade 146 and the tube scissors blade 142 slide across each other in response to the rod 144 being rotated through an arc segment to perform a scissors cutting operation between the two blades. As seen in the drawing figures, the scissors cutting operation performed by the surgical implement formed at the right hand ends of the rod and tube cut across a plane substantially parallel to the center longitudinal axis of the instrument handle 12 in the third embodiment of the instrument head 132.

A first insert 148 is inserted into the housing internal bore 136. The insert 148 has a generally cylindrical configuration with a bore hole extending through its center and with an annular flange 152 formed at its right hand end as viewed in the drawing figures. The flange 152 is press fit into a cylindrical section of the housing internal bore 136 and is thereby securely held in the bore. The internal bore of the first insert 148 is coaxial with the internal bore of the tube 138 and with the center axis of the instrument handle 12. The internal bore is dimensioned to receive the right hand end of the narrow rod 144 therethrough enabling the rod to rotate freely within the internal bore. A coil spring 154 is positioned over the cylindrical exterior of the insert 148 with the spring engaging against the annular flange 152 at one end.

A cylindrical block 156 is positioned adjacent the left hand end of the first insert 148. The block has a center bore that aligns coaxially with the center bore of the first insert 148 and the left hand end of the narrow rod 144 is received in the block center bore. A set screw 158 is received in a threaded bore extending through one side of the block 156 and is tightened down in the threaded bore to securely grip the left hand end of the rod 144 in the center bore of the block. With the rod 144 securely held to the block 156 by the set screw 158, as the block is rotated in the head housing interior 136, the rod 144 rotates with the block. A guide pin 162 is inserted into and securely held by friction engagement in a second bore hole in the side of the block 156. The guide pin 162 is employed in rotating the block through an arc segment about its center longitudinal axis in a manner to be described.

A reciprocating piston sleeve 164 is positioned over the block 156 and a portion of the first insert 148. The right hand end of the reciprocating sleeve 164 engages against the left end of the coil spring 154 positioned around the first insert 148. The exterior surface of the sleeve 164 is generally cylindrical except for a projecting guide flange 166 adjacent the right hand end of the sleeve. The guide flange serves to allow the sleeve to reciprocate in a longitudinally linear movement while preventing rotation of the sleeve about its center axis as will be explained. An angled slot 168 is cut through the exterior of the sleeve to its interior bore and the guide pin 162 of the block 156 engages in the slot. An access hole 172 is provided through the reciprocating sleeve 164 adjacent its left hand end. The access hole 172 is provided to enable access to the set screw 158 of the block 156 to tighten or release the set screw with the block received in the internal bore of the sleeve. An end cap 173 is secured to the left hand end of the reciprocating piston sleeve 164 and engages against the right hand end face of the handle piston 38. The engagement between the handle piston 38 and the piston sleeve end cap 173 causes the sleeve to reciprocate longitudinally along the center axis of the handle 12 and the instrument head 132 in response to reciprocating movement of the handle piston 38 along this axis.

A second insert 174 is press fit into the left hand end of the head housing internal bore 136. The second insert is comprised of two generally cylindrical sections 176, 178 with the first section 176 having a larger exterior diameter than the second section 178. A longitudinal slot 182 is cut through the second section 178 of the insert. The slot 182 is provided to receive the guide flange 166 of the reciprocating sleeve 164. A bore hole 184 is provided through the first section 176 of the second insert. The bore hole 184 is positioned through the insert first section so that it aligns coaxially with the bore hole through the left hand end of the reciprocating sleeve 164, providing access to the set screw of the block 156.

From the assembly of the component parts of the third embodiment of the instrument head 132 described above and shown in drawing FIGS. 10–15, it can be seen that with the instrument head releasably secured to the threaded neck 34 of the instrument handle 12, manipulation of the handle lever arms 52 laterally toward and away from the handle center axis imparts reciprocating movement to the handle piston 38 which in turn imparts reciprocating movement to the instrument head reciprocating piston sleeve 164. As the reciprocating sleeve 164 is pushed by the handle piston 38 to the right as viewed in the drawing figures, the sleeve is constrained against rotational movement by engagement of the guide flange 156 in the longitudinal slot 182 formed in the second section of the second insert. As the reciprocating sleeve 164 is pushed through the interior bore of the second insert, the coil spring 154 is compressed and the angled slot 168 of the sleeve moves relative to the guide pin 162 of the block 156. The movement of the angled slot 168 relative to the guide pin 162 causes the block to rotate through an arc segment relative to the sleeve. The engagement of the right hand end face of the block 156 with the left hand end face of the first insert 148 prevents the block from any longitudinal movement so that the block may only rotate in the instrument head interior. As the block rotates through the arc segment, the rod 144 secured in the internal bore of the block also rotates through the arc segment. Rotation of the rod 144 relative to the tube 138 causes the scissors blade 146 formed at the right hand end of the rod to slide over the scissors blade 142 formed at the right hand end of the tube, thereby performing a scissors cutting operation depicted by the arrow in FIG. 11. When the handle lever arms 52 are released from their compressed positions and allowed to resiliently bias laterally outward away from the center axis of the handle, the handle piston 38 is retracted to the left as viewed in the drawing figures and the coil spring 154 pushes the reciprocating sleeve 164 to the left. Again, the sleeve is constrained from rotational movement by engagement of the guide flange 166 in the longitudinal slot 182 of the second insert. The longitudinal, linear movement of the sleeve 164 relative to the block 156 causes the angled slot 168 of the sleeve to move relative to the guide pin 162 and rotate the block back through the same arc segment. The rotation of the block back through the arc segment also rotates the rod 144 through the same arc segment and moves the scissors blade 146 formed at the right end of the rod relative to the scissors blade 142 formed at the right end of the tube to open the blades of the scissors implement. In this manner, the surgical scissors implement formed by the blades 142, 146 at the right ends of the respective tube and rod perform a microsurgical scissors cutting operation across a plane substantially parallel to the center axis of the instrument handle 12 in the third embodiment of the instrument head 132.

Although the third embodiment of the instrument head 132 is described above as performing a scissors cutting operation by the microsurgical implement formed at the right hand ends of the tube and rod, the right hand ends of the tube and rod may be modified to form forcep jaws in place of the scissors blades disclosed. Operation of this embodiment of the instrument head would then result in the microsurgical operation of clamping the forcep jaws at the right hand ends of the tube and rod to grip an object positioned in a plane substantially parallel to the center longitudinal axis of the instrument handle and instrument head.

While the present invention has been described by reference to specific embodiments, it should be understood that modifications and variations of the invention may be constructed without departing from the scope of the invention defined in the following claims.

What is claimed is:

1. A surgical instrument comprising:
   an instrument head having longitudinally opposite first and second ends and a hollow interior extending between the first and second ends, the hollow interior including a head interior bore;
   a head piston mounted in sliding engagement with the head interior bore for longitudinally reciprocating sliding movement therein;
   an instrument tube having opposite first and second ends and a hollow interior bore extending therethrough between the first and second ends, the tube first end being received inside the head interior at the second end of the instrument head and the tube extending through and from the head interior wherein the tube second end is positioned outside the instrument head;
   an instrument rod mounted inside the tube bore for relative movement between the tube and rod, the rod having opposite first and second ends with the first rod end being received inside the head interior at the second end of the instrument head and the rod extending through and from the tube bore wherein the rod second end is positioned outside the tube bore;
   means provided in the head interior for causing relative movement between the tube and rod in response to longitudinal reciprocating movement of the head piston in the head interior bore;
   an instrument handle having a longitudinal axis and having opposite first and second ends, the handle second end being releasably attachable to the head first end, the handle having an interior bore therein coaxial to the handle axis;
   a handle piston mounted in sliding engagement with the handle bore for longitudinally reciprocating sliding movement of the handle piston in the handle bore, the handle piston being separate from but abutting against the head piston when the handle second end is attached to the head first end causing the head piston to reciprocate in the head interior bore in response to the handle piston reciprocating in the handle bore, and the handle piston and the head piston separating from each other in response to the instrument handle and the instrument head being detached from each other;
   at least one manually manipulable lever arm secured to the first end of the handle for lateral reciprocating movement of the arm relative to the handle axis; and,
   means provided in the handle for causing the handle piston to reciprocate in the handle bore in response to the lever arm being manipulated to reciprocate laterally relative to the handle axis.

2. The instrument of claim 1, wherein:
   the means provided in the head interior for causing relative movement between the tube and rod causes longitudinally linear movement between the tube and rod.

3. The instrument of claim 2, wherein:
   the second end of the instrument tube is configured as a first blade of a scissors and the second end of the instrument rod is configured as a second blade of a scissors, and relative longitudinal linear movement between the tube and rod causes the first and second scissors blades to slide adjacent each other.

4. The instrument of claim 2, wherein:
   the second end of the instrument rod is split along a center axis of the rod forming a pair of forcep jaws at the second end of the rod.

5. The instrument of claim 1, wherein:
   the means provided in the head interior for causing relative movement between the tube and rod causes rotational movement between the tube and rod.

6. The instrument of claim 3, wherein:
   the second end of the instrument tube is configured as a first blade of a scissors and the second end of the instrument rod is configured as a second blade of a scissors, and relative rotational movement between the tube and rod causes the first and second scissors blades to slide adjacent each other.

7. The instrument of claim 1, wherein:

the instrument handle is comprised of an exterior, tubular sleeve having longitudinally opposite first and second ends and having a hollow interior bore extending longitudinally therein, and the lever arm is formed from the sleeve by a pair of slots formed through the sleeve from an exterior surface of the sleeve to the sleeve interior bore, the pair of slots extending longitudinally from the second end of the sleeve to proximate the first end of the sleeve, thereby forming the lever arm between the slots as a unitary extension of the sleeve with the lever arm first end connected unitarily with the sleeve first end.

8. The instrument of claim 1, wherein:

the surgical instrument is comprised of at least a pair of lever arms, each having a longitudinal length with opposite first and second ends;

means are provided at the first end of each lever arm and at the first end of the handle for connecting each lever arm to the handle enabling the second end of each lever arm to reciprocate laterally through an arc segment relative to the handle axis; and, the instrument handle is comprised of an exterior, tubular sleeve having longitudinally opposite first and second ends and a hollow interior bore, and each lever arm is formed from the sleeve by a pair of slots formed through the sleeve from its exterior surface to the sleeve interior bore, each pair of slots extends longitudinally from the second end of the sleeve to proximate the first end of the sleeve, thereby forming the lever arms between each pair of slots as unitary extensions of the sleeve with the first ends of the lever arms connected unitarily with the sleeve first end.

9. The instrument of claim 7, wherein:

the means provided in the handle for causing the handle piston to reciprocate in the handle bore in response to the lever arm being manipulated includes at least one link member having opposite first and second ends, the link member first end being connected to the lever arm and the link member second end being connected to the handle piston.

10. The instrument of claim 8, wherein:

the means provided in the handle for causing the handle piston to reciprocate in the handle bore in response to the lever arm being manipulated includes at least a pair of link members, each link member having opposite first and second ends, each link member first end being connected to one of the lever arms and the link members' second ends being connected to the handle piston.

11. A surgical instrument comprising:

an instrument head having longitudinally opposite first and second ends and a hollow interior, the hollow interior including a head interior bore;

a head piston mounted in sliding engagement with the interior bore of the instrument head for longitudinally reciprocating sliding movement therein;

a surgical implement connected to the second end of the instrument head, the implement having means connected to the head piston for causing the implement to perform a surgical operation in response to reciprocating sliding movement of the head piston in the instrument head interior bore;

an instrument handle having a longitudinal axis and having first and second ends at opposite ends of the longitudinal axis, means provided at the handle second end for releasably attaching the handle second end to the instrument head first end, the handle having an interior bore therein coaxial to the handle axis;

a handle piston mounted in sliding engagement with the handle bore for longitudinally reciprocating sliding movement of the handle piston in the handle bore, the handle piston being separate from but abutting against the head piston when the handle second end is attached to the instrument head first end thereby causing the head piston to reciprocate in the instrument head interior bore in response to the handle piston reciprocating in the handle bore, the handle piston and the head piston separating from each other in response to the instrument handle and the instrument head being detached from each other;

at least one manually manipulable lever arm having a longitudinal length with opposite first and second ends, means connecting the lever arm first end to the handle first end for reciprocating lateral movement of the lever arm second end through an arc segment relative to the handle axis; and, means connecting the lever arm to the handle piston for causing the handle piston to reciprocate longitudinally in the handle bore in response to the lever arm being manually manipulated to reciprocate laterally through the arc segment.

12. The instrument of claim 11, wherein:

the instrument handle is comprised of an exterior, tubular sleeve having longitudinally opposite first and second ends and having a hollow interior bore extending longitudinally therein, and the lever arm is formed from the sleeve by a pair of slots formed through the sleeve from its exterior surface to the sleeve interior bore, the pair of slots extending longitudinally from the second end of the sleeve to proximate the first end of the sleeve, thereby forming the lever arm between the slots with the lever arm first end connected unitarily with the sleeve first end.

13. The instrument of claim 12, wherein:

the sleeve bore and the handle bore are coaxial with the handle bore positioned within the sleeve bore.

14. The instrument of claim 12, wherein:

the means connecting the lever arm to the handle piston includes at least one link member having opposite first and second ends, the link member first end being connected to the lever arm and the link member second end being connected to the handle piston.

15. The instrument of claim 11, wherein:

at least a pair of lever arms are connected to the handle first end, the lever arms being substantially identical to each other; and, the instrument handle is comprised of an exterior, tubular sleeve having longitudinally opposite first and second ends and having a hollow interior bore extending longitudinally therein, and the lever arms are formed from the sleeve by at least a pair of slots in the sleeve extending longitudinally from the second end of the sleeve to proximate the first end of the sleeve thereby forming the lever arms between each pair of slots with the lever arm first ends connected unitarily with the sleeve first end.

16. The instrument of claim 15, wherein:

the sleeve is formed from a resilient material giving the connection of the first end of the lever arm to the first end of the sleeve a resiliency that biases the second end of the lever arm laterally outward from the handle axis and orients the lever arm in an at rest position at an angle relative to the handle axis.

17. The instrument of claim 16, wherein:

the resiliency of the connection of the first end of the lever arm to the first end of the sleeve enables the second end of the lever arm to be manually pressed to an operative position where the lever arm is substantially parallel to the handle axis and to be resiliently biased to move in a generally pivoting movement about the connecting of the first end of the lever arm to the first end of the sleeve, through the arc segment to the at rest position of the lever arm second end relative to the handle axis.

18. The instrument of claim 11, wherein:

the surgical implement connected to the second end of the instrument head includes a tube having longitudinally opposite first and second ends and a hollow interior bore extending therethrough, the tube first end being received inside the head interior at the second end of the instrument head and the tube extending through and from the head interior wherein the tube second end is positioned outside the instrument head, an instrument rod is received inside the tube bore for relative movement between the tube and rod, the rod has opposite first and second ends with the rod first end being received inside the instrument head interior at the second end of the instrument head and the rod extending through and from the tube bore wherein the rod second end is positioned outside the tube bore, and means are provided in the head interior for causing relative movement between the tube and rod in response to reciprocating movement of the head piston in the head interior.

19. The instrument of claim 18, wherein:

the second end of the instrument tube is configured as a first blade of a scissors and the second end of the instrument rod is configured as a second blade of a scissors, and the means provided in the instrument head for causing relative movement between the tube and rod causes the first and second scissors blades to slide adjacent each other.

20. The instrument of claim 18, wherein:

the second end of the instrument rod is split along a center axis of the rod forming a pair of forcep jaws at the second end of the rod.

21. A surgical instrument comprising:

an instrument handle having a longitudinal center column with opposite first and second ends, the column having a longitudinal center axis and having means provided at the second end of the column for removably attaching the handle to an instrument head adapted to perform a surgical operation;

at least one lever arm having a longitudinal length with opposite first and second ends;

means provided at the first end of the lever arm and at the first end of the column for connecting the lever arm to the column enabling the second end of the lever arm to oscillate laterally through an arc segment relative to the column axis;

an instrument head having longitudinally opposite first and second ends with means provided at the first end of the instrument head for removably attaching the instrument head to the second end of the column and with means provided at the second end of the instrument head for performing a surgical operation;

means connected between the lever arm and the means for performing a surgical operation provided at the second end of the instrument head for operating the means for performing a surgical operation in response to oscillating lateral movement of the lever arm second end through the arc segment relative to the column axis; and, the instrument handle is comprised of an exterior, tubular sleeve having longitudinally opposite first and second ends and a hollow interior bore, the sleeve first end is connected to the column first end with the column extending through the sleeve interior bore, and the lever arm is formed from the sleeve by a pair of slots formed through the sleeve from its exterior surface to the sleeve interior bore, the pair of slots extending longitudinally from the second end of the sleeve to proximate the first end of the sleeve, thereby forming the lever arm between the slots as a unitary extension of the sleeve with the lever arm first end connected unitarily with the sleeve first end.

22. The surgical instrument of claim 21, wherein:

a second lever arm, substantially identical to the one lever arm, is formed from the sleeve by the pair of slots formed through the sleeve, the one and second lever arms being extensions of the sleeve with first ends of the lever arms connected with the sleeve first end.

23. The surgical instrument of claim 21, wherein:

the column has a longitudinal, hollow center bore and the means connected between the lever arm and the means for performing a surgical operation provided at the first end of the instrument head includes a handle piston received for longitudinally reciprocating movement in the column bore, and at least one link member having opposite first and second ends, the link member first end being connected to the lever arm and the link member second end being connected to the handle piston.

24. (amended) The surgical instrument of claim 23, wherein:

the instrument head has a hollow interior extending between the first and second ends of the instrument head and a head piston received in the instrument head interior for longitudinally reciprocating movement therein;

the means for performing a surgical operation includes an instrument tube and an instrument rod, the instrument tube extends from the second end of the instrument head, the tube has opposite first and second ends and a hollow interior bore extending therein, the tube first end is received inside the instrument head interior and the tube second end is positioned outside the instrument head;

the instrument rod is received inside the tube bore for relative movement between the tube and rod, the rod has opposite first and second ends with the first end being received inside the instrument head interior and the rod second end being outside The head; and, means are provided in the head interior for causing relative movement between the tube and rod in response to longitudinally reciprocating movement of the head piston in the instrument head interior.

25. The surgical instrument of claim 24, wherein:
the handle piston engages with the head piston when the column second end is attached to the instrument head first end causing the head piston to reciprocate in the head interior in response to the handle piston reciprocating in the column bore.

26. The surgical instrument of claim 24, wherein:
the second end of the instrument tube is configured as a first blade of a scissors and the second end of the instrument rod is configured as a second blade of a scissors, and the means provided in the instrument head for causing relative movement between the tube and rod causes the first and second scissors blades to slide adjacent each other.

27. The surgical instrument of claim 24, wherein:
the second end of the instrument rod is split along a center axis of the rod forming a pair of forcep jaws at the second end of the rod.

28. The surgical instrument of claim 21, wherein:
the instrument head has a hollow interior extending between the first and second ends of the instrument head;
the means for performing a surgical operation includes an instrument tube extending from the second end of the instrument head, the tube has opposite first and second ends and a hollow interior bore extending therein, the tube first end is received inside the instrument head interior and the tube second end is positioned outside the instrument head; an instrument rod received inside the tube bore for relative movement between the tube and rod, the rod has opposite first and second ends with the first rod end being received inside the instrument head interior and the rod second end being outside the head; and,
wherein the means connected between the lever arm and the means for performing a surgical operation causes relative movement between the tube and rod in response to oscillating lateral movement of the lever arm second end through the arc segment relative to the column axis.

29. The surgical instrument of claim 28, wherein:
the relative movement between the tube and rod is rotational movement between the tube and rod.

30. The surgical instrument of claim 29, wherein:
the second end of the instrument tube is configured as a first blade of a scissors and the second end of the instrument rod is configured as a second blade of a scissors, and relative rotational movement between the tube and rod causes the first and second scissors blades to slide adjacent each other.

31. The surgical instrument of claim 28, wherein:
the relative movement between the tube and rod is longitudinally linear movement between the tube and rod.

32. The surgical instrument of claim 31, wherein:
the second end of the instrument tube is configured as a first blade of a scissors and the second end of the instrument rod is configured as a second blade of a scissors, and relative longitudinal linear movement between the tube and rod causes the first and second scissors blades to slide adjacent each other.

33. The surgical instrument of claim 31, wherein:
the second end of the instrument rod is split along a center axis of the rod forming a pair of forcep jaws at the second end of the rod.

* * * * *